United States Patent [19]

Nikolskaja

[11] Patent Number: 5,538,620
[45] Date of Patent: Jul. 23, 1996

[54] ELECTROCHEMICAL SENSOR WITH WHICH TO MEASURE GAS CONCENTRATIONS

[75] Inventor: Elena Nikolskaja, St. Petersburg, Russian Federation

[73] Assignee: MST Micro-Sensor Technologie, GmbH, Hohenschäftlarn, Germany

[21] Appl. No.: 232,084

[22] PCT Filed: Oct. 26, 1992

[86] PCT No.: PCT/EP92/02445

§ 371 Date: Sep. 12, 1994

§ 102(e) Date: Sep. 12, 1994

[87] PCT Pub. No.: WO93/10444

PCT Pub. Date: May 27, 1993

[30] Foreign Application Priority Data

Nov. 11, 1991 [DE] Germany .................. 41 37 030.9

[51] Int. Cl.⁶ .................................................. G01N 27/26
[52] U.S. Cl. ............... 205/782; 205/782.5; 205/783; 205/785.5; 205/786; 205/783.5; 204/415; 204/431; 204/432; 204/421; 204/414; 204/430; 204/412; 422/88; 422/98

[58] Field of Search .................... 204/431, 432, 204/415, 414, 421, 430, 412, 153.17, 153.16, 153.18; 422/88, 98

[56] References Cited

U.S. PATENT DOCUMENTS

| 4,029,563 | 6/1977 | Binder et al. ............... 204/432 |
| 4,662,996 | 5/1987 | Venkatasetty ............... 204/431 |
| 5,215,643 | 6/1993 | Kusanagi et al. ............ 204/431 |

FOREIGN PATENT DOCUMENTS 4700246 of 1990 U.S.S.R.

*Primary Examiner*—Bruce F. Bell
*Attorney, Agent, or Firm*—Nikaido Marmelstein, Murray & Oram

[57] ABSTRACT

The invention concerns a novel electrochemical sensor with which to measure gas concentrations and comprising a measuring electrode and an associated electrode containing a carbonaceous material with a specific surface of at least 40 $m^2/g$ and with electrochemically active surface compounds which can be reversibly oxidized/reduced.

22 Claims, 2 Drawing Sheets

ELECTROCHEMICAL SENSOR WITH WHICH TO MEASURE GAS CONCENTRATIONS

DESCRIPTION

The present invention concerns an electrochemical sensor with which to determine the concentration of hydrogen, carbon monoxide and silane, fluorine, bromine, iodine, oxygen, sulfur dioxide, methane, ethane, ethylene, acetylene and other gases. This sensor may be used for instance in the manufacture of portable, self-powered and easily operated apparatus to measure and monitor the gas concentration.

Gas concentration analyzers to continuously monitor the surrounding medium are widely used in many fields, for instance in automatic process control, in explosion protection, ecological checking etc. Such analyzers may be electrochemical sensors. A variety of sensor types for measurement and monitoring are known.

A known kind of sensor (N.I. Globa, Razrabotka i issledvoanie elektrochimicheskich datchikov konzentratsii kisloroda i vodoroda", author's dissertation paper Leningrad Institute of Technology, 1985, pp 11–14), contains a measuring electrode and an associated electrode both located in a liquid electrolyte. The measuring electrode consists in part or in whole of a catalytically active, ie a catalytic material. The associated electrode is made of a an electrochemically active material. If this material evinces low electrical conductivity, the associated electrode will be manufactured from a mixture of this material and carbon, the carbon increasing the electrical conductivity. Illustratively the associated electrode is made of a mixture of manganese dioxide and carbon in a hydrogen sensor and is made of lead in an oxygen sensor.

When a gas of which the concentration must be measured is fed to the sensor, electrochemical oxidation or reduction (for lead or manganese dioxide) of the electrochemically active associate-electrode material takes place. This 2-electrode system generates an electric current in an external electric circuit, the current magnitude being proportional to the gas concentration. This current magnitude can be taken as a measure of the gas concentration.

The active material of the associated electrode (lead or manganese dioxide) is consumed during the chemical reactions and consequently the sensor life is limited.

Spurious measurement signals may ensue by the surface of the associated electrode being passivated by products of chemical reactions taking place on this electrode and by reaction products diffusing toward the measuring electrode, whereby sensor reliability will be degraded. To prevent such effects, sensors operating on the above stated principle must be comparatively large and must contain high quantities of material.

Another known sensor for measuring gas concentrations (Japanese patent document A 59 28358) contains a measuring electrode made from a catalytic material, further an electrolyte and an associated electrode consisting of a mixture of carbon and of an electrochemically active organic substance such as chloroquinone or monomeric and polymeric iron- and cobalt-phthalocyanine. The electrochemically active substance acts as a catalyst in the electrochemical reduction of oxygen.

The gas concentration to be measured and fed to the sensor is oxidized at the measuring electrode. Accordingly atmospheric-oxygen reduction takes place at the associated electrode or electrode reduction of especially supplied oxygen, made possible by the active components (catalysts). The catalysts are alternatingly oxidized and reduced during sensor operation. However these two reactions are not wholly reversible and consequently the catalysts are consumed and sensor life is limited. Moreover sensor reliability is poor because the surface of the associated electrode may be passivated by the oxygen-reduction products and by their diffusion toward the measuring electrode. The sensor incurs a further drawback in that the liquid electrolyte may dry out. However using a solid electrolyte in such a sensor also entails difficulties because of the need to generate a four-phase boundary "carbon-catalyst-electrolyte-oxygen".

Another restriction on using sensors of the above kind is that they can operate long-term only while being fed with oxygen, that is, only in oxygenous media or with specially implemented oxygen feed. Again, the use of liquid electrolytes entails low mechanical strength of the sensor.

A sensor developed earlier by inventor (USSR utility patent 4700246/31–25, 1990) contains a catalytically active measuring electrode and an associated electrode of chemically pure carbon with a specific surface of 1,000 to 1,700 $m^2/g$. When the sensor is in contact with a gas of which the concentration must be found, this gas will be ionized electrochemically at the measuring electrode. A charging process of the electrical double layer at the carbon-electrolyte boundary takes place at the associated electrode. The resulting current measured in an external electric circuit is proportional to the gas concentration and its magnitude is used as a measure of said concentration.

The associated electrode itself lacking any electrochemically active components, the sensor life is determined by the charging time of the electric double layer. Adequately long life can be achieved only if using chemically pure carbon with high specific surface (>1,000 $m^2/g$). In that case however the life of such a sensor of a size suitable for portable apparatus is merely about 2 years.

Moreover the manufacture of chemically pure carbon for the associated electrode is difficult because oxygenous compounds are formed at the surface during the synthesis and activation of carbon. In view of the high adsorptivity of carbon, is it practically impossible to avert interaction between the electrolyte components and the chemically pure carbon. In turn such interaction may change the potential of the associated electrode and render the signals spurious.

The object of the invention is to develop an electrochemical sensor with which to measure gas concentrations which is characterized by high reliability and life. This problem is solved by the invention by means of the sensor described below. Further objects of the invention are discussed in the following description.

One object of the invention is an electrochemical sensor to determine the concentration of a gas and comprising a housing 1, a measuring electrode 5 containing a catalytically active, i.e. a catalytic material able to ionize the gas which must be measured, an associated electrode 3 containing a carbonaceous material, and an electrolyte in contact with the measuring and associated electrodes, the invention being characterized in that the carbonaceous material in the associated electrode evinces a specific surface of at least 40 $m^2/g$ and contains electrochemically active surface compounds which can be oxidized and reduced reversibly.

The catalytic material of the measuring electrode must be resistant to the electrolyte and furthermore must catalyze the reaction of the gas to be quantified. Illustratively platinum may be the catalytic material for a plurality of sensors. Furthermore the catalytic material may be prepared from carbon for a fluorine sensor and from gold for an oxygen sensor. The measuring electrode may consist in whole or in part of the catalytic material, that is, a platinum wire may be used, for instance, or a platinum mesh, or an electrode merely coated with platinum.

The associated electrode of the sensor of the invention contains a carbonaceous material, that is, it consists in whole or in part of the above stated carbonaceous material. As a rule the electrochemically active compounds on the surface of the associated electrode are oxygenous compounds formed on said surface during the manufacture of the carbonaceous material. Such compounds can be oxidized and reduced in reversible manner. Illustratively these are compounds of the hydroquinone/quinone type.

When current is passing through the associated electrode of the sensor of the invention, the electric double layer at the electrode-electrolyte boundary will be charged and thereby a reversible oxidation/reduction of the electrochemically active compounds on the surface of the associated electrode will take place. Preferably the carbonaceous material in the associated electrode is activated carbon with oxygenous, electrochemically active surface compounds. Because of the high specific surface and the chemical properties of activated carbon, the capacitance of the associated electrode and the number of active surface compounds are very high. As a result, when the sensor is operated, the potential of the associated electrode changes very slowly and therefore remains very long in the range of the electrochemical stability of the electrolyte.

When gas is supplied, a reaction of the gas of which the concentration must be determined takes place at the measuring electrode. The associated electrode experiences the charging of the double layer and reversible oxidation and reduction of the surface compounds occur. If the electrodes are connected by terminals to an external electrical circuit, the current present in it can be used as a measure of the gas concentration.

The life of the sensor of the invention depends on the double-layer capacitance and on the number of electrochemically active surface compounds. The larger the specific surface of the associated electrode, the longer again the sensor life.

The electrochemical properties of the active surface compounds of the activated carbon being used preclude electrode passivation or diffusion of the reaction products toward the measuring electrode. Consequently sensor reliability is high.

The sensor of the invention does not require the presence of oxygen at the associated electrode, and thereby the sensor may be used also in oxygen-free media and sensor reliability and mechanical strength are thus enhanced.

The sensor life is substantially extended because of the presence of reversibly reducible or oxidizable chemical surface compounds in the carbonaceous material of the associated electrode, without entailing increasing its weight and size. Therefore the sensor of the invention can be designed to be portable and self-powered.

As a rule no chemical interactions take place with the electrolyte in a carbonaceous material containing chemical surface compounds and therefore unanticipated changes in the potential of the associated electrode are precluded, thereby again increasing sensor reliability.

Already when using activated carbon with low specific surface (for instance 40 $m^2/g$) and with electrochemical active surface compounds allows making sensors evincing adequate properties. Using activated carbon with high specific surface (1,000–3,000 $m^2/g$) allows making very-long life sensors without the need to enlarge them.

Advantageously the associated electrode of the sensor of the invention shall be housed inside a hermetically sealed chamber. Thereby the associated electrode is protected against contamination contact and the sensor life is consequently increased. Advantageously too the electrolyte shall be imbedded in a solid matrix. As a result the electrolyte cannot dry out and the sensor life is lengthened. Moreover the sensor's mechanical strength is increased thereby. Illustratively an electrolyte can be imbedded into a solid matrix by adding polymerizing monomers (for instance methylmethacrylate) to said electrolyte. Thereupon the mixture of electrolyte and monomers in its liquid state is made to contact the associated electrode. Next the monomers may be polymerized to form a solid matrix block imbedding the electrolyte and the associated electrode.

In many cases and especially regarding a narrow range of diffusion boundary flow, a sensor with three electrodes may be used advantageously. Aside the measuring electrode and the associated electrode, such a sensor also contains a reference electrode. This reference electrode serves to keep the measuring electrode at an essentially constant potential (namely in the range of diffusion boundary flow). The reference electrode may consist of a catalytic material, for instance of the same material as the measuring electrode. Moreover the reference electrode shall evince a large surface to avert polarization. The reference electrode is inserted into the electrolyte, for instance between the measuring and associated electrodes. When using such a three-electrode sensor, the same processes take place at the measuring and associated electrodes as with a two-electrode sensor.

In a further preferred embodiment mode of the invention, the sensor also may comprise one or more supplement electrodes. Using such a supplement electrodes allows sensor regeneration while being operated by discharging the associated electrode. Such a voltage is applied across the associated and the additional electrode that processes will take place at the associated electrode which counteract the charging of the associated electrode in normal sensor operation. Operation of a sensor with a supplement electrode is comprehensively described in the discussion relating to FIG. 2.

In yet another preferred embodiment mode of the invention, the sensor may comprise several, for instance two, measuring electrodes. The design of such a sensor is similar to that using a supplement electrode, except for a second measuring electrode comprising a diffusion membrane being used instead of the supplement electrode. A voltage required for the concentration measurement of the particular gas is applied across this measuring electrode and the associated electrode. The second measuring electrodes operates on the same principle as the first. The selection of the catalytic material and voltage determines which reaction takes place at the second measuring electrode, that is, in particular which gas shall be reacted.

Advantageously with respect to this embodiment mode, the oxidation of a gas to be quantified shall take place at one of the measuring electrodes and the reduction of a second gas at the second electrode. In this case the associated electrode is charged during the operation of the first measuring electrode while the associated electrode is discharged during operation of the second measuring electrode. As a result the life of the electrochemical sensor is considerably extended because the associated electrode no longer is being charged during alternating and/or simultaneous operation of the measuring electrodes. Accordingly the second measuring electrode serves to measure a second gas concentration and as a supplement electrode to discharge the associated electrode.

Another object of the present invention is a method employing the electrochemical sensor of the invention to determine the concentration of one or more gases. The method of the invention allows quantifying arbitrary gases provided they be reacted at the catalytic measuring electrode. Illustratively suitable gases are hydrogen, fluorine, chlorine, bromine, iodine, oxygen, sulfur dioxide, silane, carbon monoxide, nitrogen dioxide, methane, ethane, ethylene and acetylene. Preferred gases are hydrogen, silane, carbon monoxide or oxygen. When two measuring electrodes are used, two different gases (for instance hydrogen and oxygen) can be quantified simultaneously.

In a preferred mode of implementation, the method of the invention is carried out by connecting the electrochemical sensor by terminals to an external electric circuit, by adjusting a suitable external voltage for instance from 0.1 to 0.6 volts across the sensor electrodes and by measuring the current proportional to the concentration of the monitored gas in the outside part of the electric circuit. When monitoring hydrogen, a sensor is used for instance which comprises a platinum measuring electrode, an activated carbon associated electrode with a specific surface of 1,000–1,700 $m^2/g$ and an electrolyte based on a strong mineral acid (for instance $H_2SO_4$, $H_3PO_4$ etc.), an external voltage across the electrodes of about 0.3 volts being applied. The electrolyte may be imbedded into a solid matrix.

Another advantage in gas monitoring using a sensor of the invention is that this sensor can be regenerated following a predetermined time of operation by reversing the electrode polarization by applying an external voltage. Another object of the invention is a solid electrolyte especially suitable for an electrochemical sensor, and in particular that of the invention. This solid electrolyte consists of a polymer incorporating an electrolyte solution. It is prepared by mixing a suitable polymerizing monomer or mixture of monomers with a liquid electrolyte, for instance an aqueous or aqueous/ organic solution of acids, salts or bases, and then polymerizing. Conventional auxiliaries such as initiators, catalysts, cross-linking agents etc. may be used for polymerization. Within the scope of the sensor of the invention, a solid electrolyte is preferred which is prepared by polymerizing a mixture of methylmethacrylate being the monomer, azobis(isobutyronitrile) being the initiator and an acid or a mixture of acids. Appropriate acids for instance are sulfuric acid, trifluoromethane sulfonic acid and phosphoric acid, or a mixture thereof.

BRIEF DESCRIPTION OF THE DRAWINGS

Several preferred embodiment modes of the sensor of the invention are described below. The attached FIG. 1 is a schematically simplified vertical section of a first embodiment of a sensor of the invention. As shown in FIG. 1, the sensor comprises a housing 1 made of an inert dielectric material such as Teflon® or plexiglass.

Figure 1:
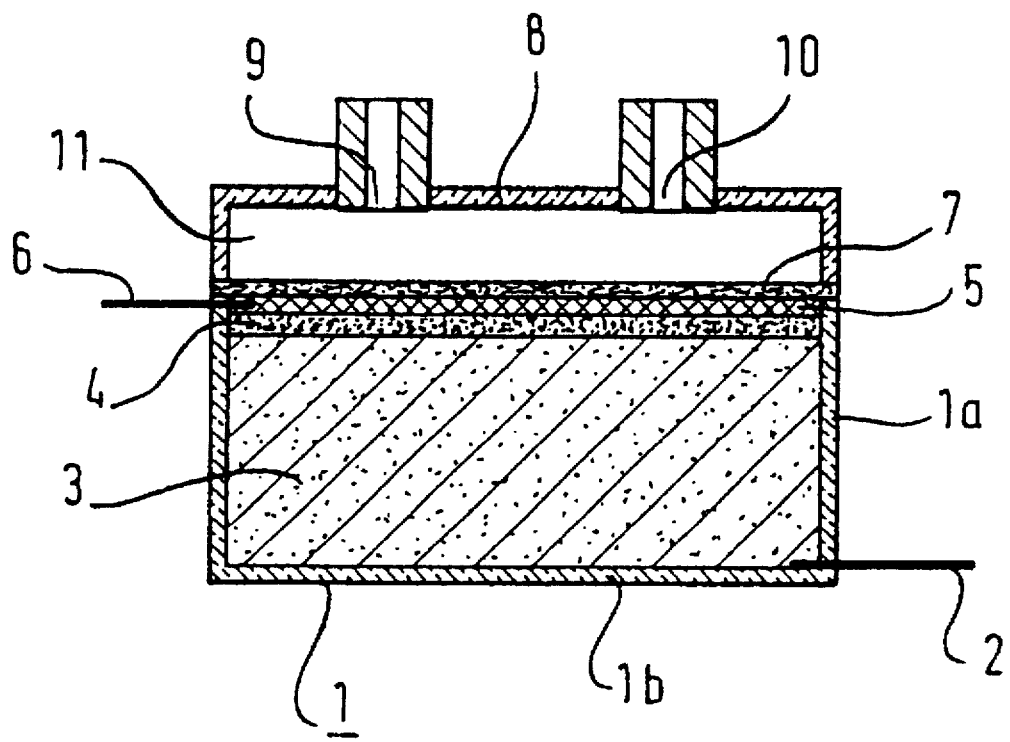
FIG. 1 is a vertical section of a first embodiment of the sensor of the present invention.

Illustratively the housing dimensions may be 20 mm in diameter and 40 mm in height. Two apertures for electrode terminals 2, 6 are present in the cylindrical sidewall 1a. The terminal wire 2 connects to the associated electrode in the finished sensor and rests on the housing bottom 1b, being made to pass through an aperture. The associated electrode 3 prepared from activated carbon with electrochemically active surface compounds is inserted into the housing. The specific surface of the associated electrode is 1,000 to 1,700 $m^2/g$, that is, its porosity is very high. The associated electrode is impregnated with the liquid electrolyte. The electrolyte consists of a mixture of polymerizing monomers such as methylmethacrylate and a polymerization initiator such as azo-bis(isobutyronitrile) and an ionically conducting substance (for instance an acid in the case of an $H_2$ sensor) and is poured into the housing and left to stand for about 30 minutes. During that time the liquid may enter the pores of the associated electrode. Thereafter the associated electrode is compressed by a plunger, and the housing with the associated electrode is placed into a heating apparatus. Incomplete prepolymerization takes place in the heating apparatus at a particular appropriate temperature (for instance 120° C.) within an appropriate time interval (for instance 2 h), resulting in increased electrolyte viscosity. The extent of this polymerization can be controlled by the external factors (time, temperature, where called for pressure), by the initiator concentration and where called for by adding a polymerization inhibitor. A "block" consisting of the associated electrode, the electrolyte and the terminal wire is made inside the housing by the said prepolymerization. Next the housing with the associated electrode block is removed from the heating apparatus and a separator 4 is laid on the block. The separator assumes the shape of a disk about 50 μ thick and with a diameter corresponding to that of the housing. Preferably the separator is made of a porous polymer resistant to the electrolyte being used, for instance a polypropylene.

Next the catalytic measuring electrode 5 is placed on the separator. Illustratively the measuring electrode may be made in the form of a platinum mesh about 50 μ thick and with a diameter corresponding to that of the separator. The terminal wire 6 connected to the measuring electrode passes through one of the housing apertures. The separator and the measuring electrode are pressure-joined to the associated electrode block, whereby the separator becomes impregnated with the electrolyte and the measuring electrode is moistened by it. The sensor so prepared is again placed into the heating apparatus where presently complete electrolyte polymerization takes place under the appropriate conditions (for instance at 110° C. within 1 h).

Thereupon a gas-permeable diffusion membrane 7 preferably consisting of a polymer such as teflon is placed on the measuring electrode. This membrane shall lie snugly against the electrode. A cap 8 is placed on the housing and presses the membrane against the measuring electrode. Illustratively the cap is made of the same material as the housing. The cap comprises intake apertures 9, 10 allowing the gas to reach the sensor. Where called for the cap also may comprise fasteners for the conduits feeding and evacuating a gas flow to and from the sensor.

A gas cell 11 is present between the cap 8 and the diffusion membrane 7. The cap, the membrane and the housing are solidly joined together, instance bonded. In this manner the associated electrode will be within a sealed chamber enclosed by the housing and the separator. The terminal wires are hooked-up to an external electrical circuit (omitted) containing an ammeter and a voltage source.

In another possible embodiment mode of the sensor, the electrolyte is solid instead of liquid. In this case the associated electrode is impregnated with the electrolyte and a rigid, porous membrane illustratively made of the same material as the housing is placed into the housing. A separator and the measuring electrode are then laid on this membrane as in the above described sensor. No polymerization takes place in the heating apparatus. In the other respects the sensor manufacture takes place in the same manner as for the sensor with the solid electrolyte.

In sensor operation, the gas mixture containing the monitored gas passes through the apertures 9, 10 into the gas cell 11 and diffuses through the diffusion membrane 7 to the measuring electrode 5. The membrane assures steady gas-mixture feed to the measuring electrode. The measuring-electrode potential may be selected in such a way that only the monitored gas is being reacted. The terminal wires are connected to the external voltage source which supplies the required potential difference relative to the associated electrode 3.

Because of its high capacity, the associated electrode potential changes only very slowly and thus the potential difference will be kept constant, hence the measuring electrode potential will also change only very slowly. The measuring electrode potential is in the diffusion current range of the gas reaction. That gas arriving at the measuring electrode will be reacted, the ions formed in the electrolyte during the reaction migrate to the surface of the associated electrode. As a result a current is set up in the external electric circuit. While allowing the ions through, the separator on the other hand precludes electrical contact between the two electrodes. Because of the charge migration to the associated electrode, the electrical double layer at the boundary between the electrolyte and the associated electrode will charge up. The ions are adsorbed at the surface of the associated electrode.

The processes taking place in the electric double layer are comprehensively described in the Damaskin & Petry book "Vvedenie v elektrochimicheskuju kinetiku", 1975, pp 105–130, Moscow High School.

The associated electrode potential changes as the double layer is being charged. Upon reaching corresponding potential values, reversible oxidation/reduction of the chemical surface compounds take place at the associated electrode surface. These processes are described in M R Tarasevitsch "Elektrochimia uglerodnych materialov", 1984, p 253, "Nauka", Moscow.

The current in the external electric circuit is proportional to the concentration of the gas being reacted at the measuring electrode in the presence of ion formation. When there is a current, the charge at the electric double layer increases with time and the associated electrode potential changes.

The electrochemical stability of the electrolyte being used determines the admissible change in potential. When the associated electrode potential exceeds the potential of electrolyte dissociation, the current in the external electric circuit no longer will be proportional to the gas concentration. This leads to spurious gas concentration measurements, that is, the gas concentration can be reliably determined only as long as the associated electrode potential remains in the admissible range. Sensor life corresponds to the time wherein the associated electrode potential does not change enough to exceed the maximum allowable change.

The sensor life is computed below. The double-layer capacitance C corresponds to the charge $q_c$ which must be supplied to the associated electrode to change its potential by one unit, $$C = q_c/\phi \quad (1).$$

If only the double layer were being charged at the associated electrode, the charge supplied by the current I during time $t_c$ would change the associated electrode potential by $\Delta\phi$, $$C = (It_c)/(\Delta\phi) \quad (2)$$

If $\Delta\phi$ is the maximum allowable change in potential and if there is only charging of the double layer, the sensor life is then given by $$t_c = (C\Delta\phi)/I \quad (3).$$

The double-layer capacitance is proportional to the magnitude S of the associated electrode surface ($C = K_c S$, with $K_c$ being a constant of proportionality), and it follows from eq. (3) that $$t_c = (K_c S \Delta\phi)/I \quad (4).$$

Moreover reversible oxidation/reduction of chemical surface compounds is taking place at the associated electrode. These Faraday processes are as follows $$q_f K_f = \Delta m \quad (5)$$

where $\Delta m$ = the reacted amount of material; $K_f$ = a proportionality constant; $q_f$ = the charge consumed for reduction/oxidation.

The charge qe follows from the current I and the time in which the Faraday processes took place, namely $q_f = It$, whereby $$It_f K_f = \Delta m \quad (6).$$

Various surface compounds are present on the associated electrode and relate to different reduction/oxidation potentials. These values fall within the permissible range $\Delta\phi$. The Faraday capacitance (the capacitance linked to the sequence of the Faraday processes) is higher by an order of magnitude than that of the double layer. Therefore the change in the associated electrode potential when reducing/oxidizing the surface compound will be much slower than during merely one charging of the double layer. The potential remains practically unchanged over some time in many ranges of the charging curve (potential function of the supplied charge). The Faraday processes lead to the associated-electrode potential remaining much longer in the permissible range and to the sensor life being much extended.

Once a specific surface compound has been entirely oxidized or reduced, the potential will change again according to eq. 2 until a value is reached at which another surface compound shall be oxidized/reduced.

Accordingly the associated-electrode potential varies by eq. 2 with interruptions caused by the Faraday processes.

The following applies to a surface compound i:

$$It_{fi} K_{fi} = \Delta m_i \quad (7)$$

where $t_{fi}$ is the time of reducing or oxidizing the surface compound i; $K_{fi}$ is a proportionality constant for the surface compound i and $\Delta m_i$ is the reacted quantity of the surface compound i.

The total time during which the Faraday processes take place is given by:

$$\sum_i t_{fi} = \sum_i \frac{\Delta m_i}{IK_{fi}} = \frac{1}{I} \sum_i \frac{\Delta m_i}{K_{fi}} \quad (8)$$

The quantity of the surface compounds is proportional to the surface S of the associated electrode $$\Delta m_i = K_i S \quad (9)$$

whereby $$\sum_i t_{fi} = \frac{1}{I} \sum_i \frac{K_i S}{K_{fi}} = \frac{S}{I} \sum_i \frac{K_i}{K_{fi}} \quad (10)$$

The sensor life t is given by the sum $$t = t_c + t_f \quad (11)$$

from which it follows that $$t = \frac{K_c S \Delta \phi}{I} + \frac{S}{I} \sum_i \frac{K_i}{K_{fi}} = \frac{S}{I} \left( 9 K_c \Delta \phi + \sum_i \frac{K_i}{K_{fi}} \right) \quad (12)$$

The sensor life is the longer the larger the surface of the associated electrode, the permissible change in potential, the quantity of surface compounds and the smaller the current through the electrode.

The current magnitude can be adjusted by material selection, by the design and the position of the membrane 7 as well as of the measuring electrode 5. These parameters must be selected in such a way that the required measurement accuracy and the corresponding range of measurement shall be assured. As a rule the current is in the µa range.

The permissible change of the associated-electrode potential depends on the electrochemical stability of the electrolyte. This change amounts to 0.4 to 0.6 volts for the solid electrolytes used.

For a specific surface of 1,000–1,700 m² of the activated carbon and an associated-electrode weight of about 10 g, the associated-electrode surface will be very large, up to several thousand square meters. Such a surface results in very high double-layer capacitance (several thousand farads F); for instance for activated carbon with a specific surface of 1,500 m²/g, the specific capacitance will be 400 F/g.

For an associated electrode of 10 g of activated carbon, a permissible potential change of 0.4 and a current of 20 µa, eq. 3 results in $$t_c = \frac{400 \times 10 \times 0.4}{20 \times 10^{-6}} = 80 \times 10^6 \, s \approx 20,000 \, h$$

The quantity of chemical surface compounds may be estimated. According to M R Tarasevitsch ("Elektrochimia uglerodnych materialov", 1984, Nauka, Moscow, p 35), the maximum oxygen content in activated carbon is 0.5 to 3 mmole/g. Oxygen is present at the surface of the activated carbon among other forms in that of compounds such as quinone-hydroquinone on the surface of the activated carbon as shown by the empirically determined reversibility of electrochemical processes, known from the literature (catalogue, NEC, Japan, 1982) in the potential range used. Assuming that about half the quantity of oxygen is contained in such compounds, this quantity may be a maximum of about 3 mmole/g of the activated carbon (the functional quinone group contains one oxygen atom). Reduction/oxidation of the functional group of compounds of the quinone-hydroquinone type being related to the transfer of one electron, the quantity of charge required for the reduction/oxidation of such compounds is given by $q_f = 26.8 \, \text{ampx} h \, \text{mole}^{-1} \times 3 \times 10^{-3} \, \text{mole/g} = 0.08 \, \text{ampx} h/g$.

From $$q_f = I t_f, \, ie, \, t_f = q_f / I \quad (13),$$

there results for the above example and for an electrode weight of 10 g, $$t_f = \frac{0.08 \times 10}{20 \times 10^{-6}} = 40,000 \, h$$

Using eq. 11, $t = t_c + t_f = 20,000 + 40,000 = 60,000 \, h$.

in other words, t>6 years.

When the carbon specific surface is 2,000 m²/g, such an estimate provides a life of about 80,000 h or about 9 years.

Using activated carbon with higher specific surface increases sensor life but entails higher costs. The known maximum specific surface of activated carbon is about 3,000 m²/g (B Elwin, S Stail, "Nositeli i naniesiennyie katalisatory. Teoria i praktika", 1969, Chimia, Moscow, p 111).

Using activated carbon with a specific surface of 40 to 1,000 m²/g results in sensors having a life that of most known ones (about 1 year). Illustratively the activated-carbon associated electrode with a specific surface of 40 m²/g and a weight of 50 g has a life of about 8,000 h (less than 1 year).

The electrochemical properties of the chemical surface compounds preclude passivation of the associated electrode and also diffusion of the reaction products to the measuring electrode, whereby sensor reliability is assured. The electrochemical reaction participated in by the chemical surface compounds are reversible.

A known system, the so-called super-capacitor (1982 Nippon Electric catalogue, Japan) contains two activated carbon electrodes and is used as a capacitor of very high capacitance. The same processes take place at both electrodes as described above for the associated electrode. Because of the reversibility of the electrochemical processes at the activated carbon electrodes and the consequently unlimited number of charge-discharge cycles, capacitor life is unlimited. 15,000 cycles were achieved without parameter change.

According to data from the literature and based on experiment, the sensors of the invention can be regenerated after the end of service life by applying an external voltage and reversing the electrode polarization. Thereupon reactions which are the reverse of the above described electrochemical ones take place at both electrodes.

For instance in a hydrogen sensor, hydrogen is produced from the protons of the electrolyte ($2H^+ + 2e^- \rightarrow H_2$) at the measuring electrode upon polarization reversal. The discharge of the electrochemical double layer and an oxidation of the reduced chemical surface compounds or a reduction of the oxidized chemical surface compounds occurring during sensor use take place at the associated electrode. Once the quantity of charge accumulating in the reverse direction corresponds to that which was achieved during sensor operation, the associated electrode will again be in its initial state as regards charge and potential. During the charging procedure, that amount of hydrogen will be generated at the measuring electrode which corresponds to the quantity of hydrogen reacted during operation.

The sensor returns to its initial state and is usable again to determine hydrogen concentrations.

The processes at the measuring electrode in the hydrogen sensor being reversible, theoretically the number of "operation-regeneration" cycles is unlimited, in other words, theoretical sensor life also is unlimited provided the sensor always be regenerated. The associated electrode withstanding at least 15,000 operation-regeneration cycles, the ability to regenerate the sensor is determined by the measuring electrode. Illustratively the number of cycles for an oxygen sensor is about 50.

Compared with all known electrochemical gas concentration sensors, the sensor life is much lengthened by the ability to regenerate. Accordingly the sensor of the invention shall advantageously contain species of electrolyte ions which are also produced in the gas reaction at the measuring electrode. When such an electrolyte is used, the composition and the concentration of the electrolyte will practically remain constant. For instance an electrolyte containing protons will be used in the hydrogen sensor ($H_2 \rightarrow 2H^+ + 2e^{30}$), an electrolyte containing fluorine ions will be used in the fluorine sensor ($F_2 + 2e^+ \rightarrow 2F^x$), an electrolyte containing chlorine ions will be used in the chlorine sensor ($Cl_2 + 2e^+ \rightarrow 2Cl^-$).

However other electrolytes also may be used, for instance an electrolyte containing $F^-$ ions may be used to determine chlorine concentrations. But this leads to changing the electrolyte composition during the gas reaction and may result in shortening sensor life and creating spurious signals on account of the change in the equilibrium potential of the measuring electrode.

Figure 2:
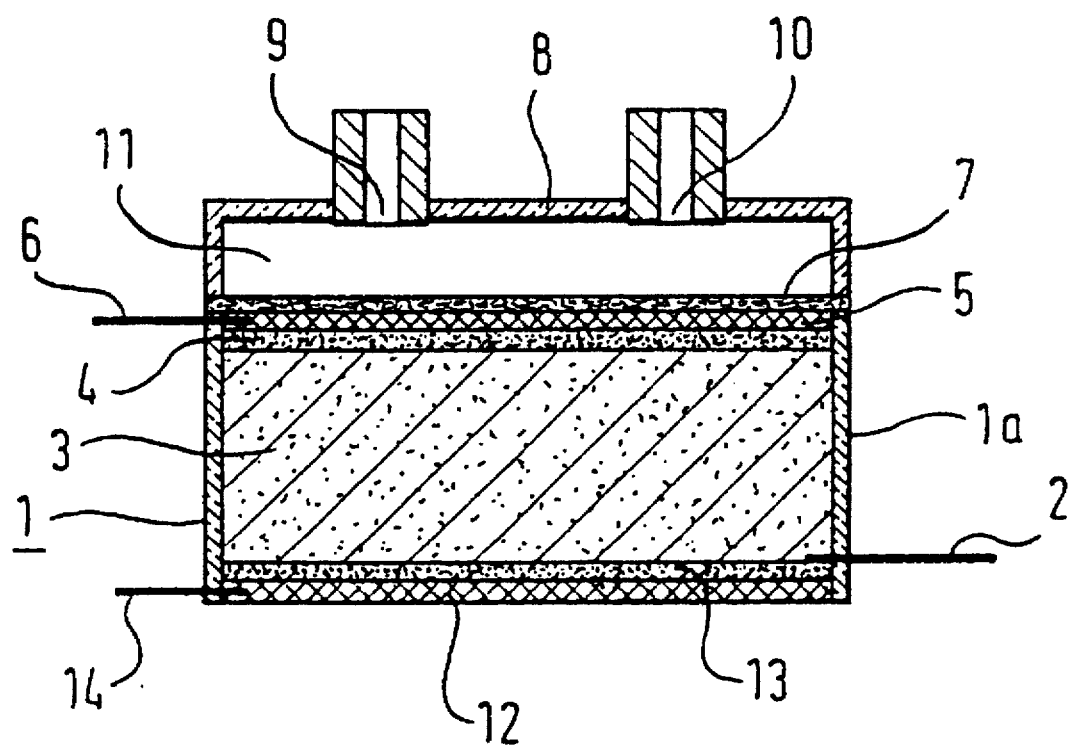
FIG. 2 is a vertical section of a second embodiment of a sensor of the present invention which, besides the measuring and associated electrodes, also contains a supplement electrode.

FIG. 2 shows a second embodiment mode of the sensor of the invention which besides the measuring and associated electrodes also contains a supplement electrode. In this mode the sensor can be regenerated while being in operation. The reference numerals used for FIG. 2 correspond to those of FIG. 1.

The sensor housing of FIG. 2 lacks a backwall such as 1b in FIG. 1. Instead the sensor contains a supplement electrode 12 kept by a separator 13 from the associated electrode. The supplement electrode may be made of a catalytic material, for instance being a platinum mesh. The terminal wire 14 sets up the contact with the supplement electrode. A voltage is applied across the associated and supplement electrodes during sensor operation. The gas concentration is measured in the manner described for a sensor lacking a supplement electrode. The supplement electrode implements sensor regeneration while this sensor is operating. For that purpose the voltage across the associated and supplement electrodes is selected in such a way that processes shall take place in the associated electrode which are opposite those of normal sensor operation (in relation to the measuring electrode). For instance if the associated electrode acts as cathode relative to the measuring electrode, as a result of which the processes of charging the electric double layer and reducing the surface compounds take place while the sensor is operating, then the associated electrode will act as anode relative to the supplement electrode, whereby discharge of the electric double layer and oxidation of the surface compounds at the associated electrode shall take place simultaneously. An electrochemical reaction, for instance reduction of atmospheric oxygen, or hydrogen generation from the electrolytes, will simultaneously take place at the supplement electrode. The rates of such processes depend on the voltage across the supplement and associated electrodes. Advantageously the voltage is selected in such manner that the current in the external circuit between these electrodes is of the same value but of opposite direction than the central current between the measuring and associated electrodes.

In this manner there will be simultaneously charging and discharging of the associated electrode during sensor operation. As a result sensor life is considerably extended. This life is determined by the permissible change in the associated electrode potential. The associated electrode potential changes much more slowly when using the supplement electrode. The life of such a sensor with supplement electrode is determined by the possible change of electrolyte composition in the electrochemical reactions at the measuring and supplement electrodes. In many instances however the theoretical life of such a sensor is unlimited, for instance if hydrogen generation occurs at the supplement sensor of a hydrogen sensor, then the electrolyte composition will remain constant. The following reactions take place in such a sensor:

At the measuring electrode

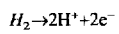

At the supplement electrode

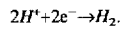

The design including the supplement electrode extends the sensor life and/or allows decreasing the sensor size (quantity of activated carbon) without negatively affecting sensor life.

The invention is elucidated by the following Examples.

EXAMPLE 1

A hydrogen sensor of the invention was manufactured and tested. The sensor housing was polyethylene. The associated electrode was an activated carbon fabric 40 μ thick with a specific surface of 1,500 m²/g. Its diameter was 20 mm. The total electrode weight was 2.3 g. The measuring electrode was a platinum mesh and its diameter was 19 mm. The separator was polypropylene. A liquid electrolyte was used (38% sulfuric acid). The diffusion membrane was a polyethylene foil 20 μ thick. The sensor inside diameter was 24 mm, its height was 20 mm and its weight was 3 g. A micro-ammeter and a voltage source were present in the external electric circuit. The permissible change in associated electrode potential in the electrolyte was 0.4 volts.

A mixture of gaseous hydrogen and oxygen was used to supply the gas.

The hydrogen concentration was known and as high as 48%. For an $H_2$ concentration of 4% and a polarization voltage of +0.3 v (measuring electrode relative to the associated electrode), the current was 10 μa. At the specific activated carbon surface of 1,500 m²/g. The the specific capacitance was about 400 F/g, and the life t then could be estimated from eqs. 3, 11, 13:

$$t = \frac{400 \times 2.3}{10 \times 10^{-6} \times 3,600} + \frac{0.08 \times 2.3}{10 \times 10^{-6}} \approx$$

$$10,000 \text{ h} + 18,400 \text{ h} = 28,400 \text{ h}$$

that is, more than 3 years.

Furthermore a hydrogen sensor of the invention was manufactured with a solid electrolyte and then tested. The housing was polymethylmethacrylate (plexiglass). The associated electrode was activated carbon powder with a specific surface of more than 1,500 m²/g. The weight of the associated electrode was 1.8 g. The solid electrolyte was a mixture of methacrylate as the monomer, azo-bis(isobutyronitrile) the initiator and sulfuric acid (38%) by polymerizing at raised temperature. The measuring electrode, the separator and the membrane were made in the manner described for the above sensor. The permissible change in the associated electrode potential was 0.6 volts. At a hydrogen concentration of 4% and a polarization voltage of +0.3 volts, the current was 12 μa. The sensor life was estimated as follows:

$$t = \frac{400 \times 2.3 \times 0.4}{10 \times 10^{-6} \times 3600} + \frac{0.08 \times 2.3}{10 \times 10^{-6}} \approx$$

$$10{,}000 \text{ h} + 12{,}000 \text{ h} = 22{,}200 \text{ h}$$

that is, about 2½ years.

Following 500 h of gas feed, the sensor was regenerated by reversing the direction of the polarizing voltage.

EXAMPLE 2

A sensor of the invention with measuring, associate and reference electrodes for measuring carbon monoxide concentrations was made and tested. The sensor contains a solid electrolyte, a measuring, an associate and a reference electrode. The solid electrolyte was prepared by polymerizing a mixture of methylmethacrylate as the monomer, azo-bis(isobutyronitrile) as the initiator, and phosphoric acid, at raised temperature. The measuring and reference electrodes were platinum tubes coated with a teflon membrane. Then the associated electrode and the separator were prepared in the manner described for Example 1. The reference electrode is present between the measuring and the associated electrode and is kept apart from both by the separator. The permissible change in the associated electrode potential in the electrolyte used was 0.4 volts. The measuring electrode potential was kept constant by a potentiometric circuit relative to the reference electrode potential. For the bias used (potential difference between the measuring and reference electrodes), namely 0.1 volts, and for a CO concentration of 30 ppm in air, the sensor current was about 1.5 μa. The sensor life was estimated in the manner computed in Example 1, namely $$t = \frac{400 \times 2.3 \times 0.4}{1.5 \times 10^{-6} \times 3{,}600} + \frac{0.08 \times 2.3}{1.5 \times 10^{-6}} =$$

$$68{,}000 \text{ h} + 120{,}000 \text{ h} \; (>20 \text{ years}).$$

EXAMPLE 3

A hydrogen sensor of the invention with a supplement electrode was made and tested. The sensor contains a measuring and an associated electrodes and a solid electrolyte such as prepared in Example 2. The supplement electrode was a platinum mesh. At the employed bias of −0.25 volts between the measuring and the associated electrodes and for a hydrogen concentration of 200 ppm, a cathode current of −550 na (relative to the associated electrode) passes through the external electrical circuit. A voltage of +0.15 volts was applied across the supplement and the associated electrodes, causing an anode current of 500 na (relative to the associated electrode). Accordingly charging and simultaneous discharging of the associated electrode take place in parallel in this sensor. The electrolyte composition remains constant and theoretically the life of such a sensor is unrestricted.

EXAMPLE 4

A sensor of the invention with two measuring electrodes was made and tested. The hydrogen concentration is determined at one of the measuring electrodes, and the oxygen concentration at the other. The sensor contains the solid electrolyte described in Example 2. The diffusion membrane was a polyethylene foil 20 μ thick for the hydrogen measuring electrode and 30 μ thick for the oxygen measuring electrode. At the applied voltage of +0.3 volts across the hydrogen and the associated electrodes and for an $H_2$ concentration of 400 ppm, there is a current of 4.5 μa in the external electrical circuit. At a voltage of −0.2 volts across the oxygen measuring electrode and the associated electrode and for an oxygen concentration of about 20.8%, a current of about 5 μa is present in the external electric circuit. In this manner charging and discharging of the associated electrode takes place in parallel. The effective current causing charging of the associated electrode is the difference of those two currents and amounts to 5 μa −4.5 μa =0.5 μa, the currents relating to the oxidation of $H_2$ and to the reduction of $O_2$ being in opposite directions. The life of such a sensor is given by $$t = \frac{400 \times 1 \times 0.4}{0.5 \times 10^{-6} \times 3{,}600} + \frac{0.08 \times 1}{0.5 \times 10^{-6}} =$$

$$89{,}000 \text{ h} + 160{,}000 \text{ h} = 250{,}000 \text{ h}$$

EXAMPLE 5

Instead of one acid, the sensor of the invention also may contain a mixture of acids. A two-electrode sensor of the invention for determining carbon-monoxide concentrations was made and tested. The solid electrolyte was prepared at raised temperature by polymerization from a mixture of methylmethacrylate as the monomer, iso-bis(isobutyronitrile) as the initiator and trifluoromethane sulfonic acid and phosphoric acid. Such an electrolyte evinces very low hygroscopy and therefore is appropriate especially for sensors comprising porous diffusion membranes. The permissible change of the associated electrode potential is 0.2 volts for this electrolyte.

I claim:

1. An electrochemical sensor to determine a gas concentration of a gas to be quantified, comprising a housing, a measuring electrode located within the housing and comprising a catalytic material which causes a reaction of the gas to be quantified, an associated electrode located within the housing and comprising a carbonaceous material, and an electrolyte in contact with the measuring and associated electrodes, wherein the carbonaceous material in the associated electrode has a specific surface of at least 40 m²/g and comprises reversibly oxidizable or reducible electrochemically active surface compounds.

2. The electrochemical sensor defined in claim 1, wherein the carbonaceouse material in the associated electrode is a porous, activated carbon with oxygenous, electrochemically active surface compounds.

3. The electrochemical sensor defined in claim 1, wherein the carbonaceous material in the associated electrode evinces a specific surface of 1000 to 3000 m²/g.

4. The electrochemical sensor defined in claim 1, wherein the catalytic material in the measuring electrode is selected from the group consisting of platinum, carbon and gold.

5. The electrochemical sensor defined in claim 1, wherein the electrochemically active surface compounds comprise hydroquinone or quinone.

6. The electrochemical sensor defined in claim 1, wherein the electrolyte is embedded in a solid matrix.

7. The electrochemical sensor defined in claim 1, wherein the housing comprises apertures for electrode terminals and a gas cell having intake apertures, the gas cell allowing the gas to be quantified to contact the measuring electrode.

8. The electrochemical sensor defined in claim 1, further comprising an ion-permeable separator located between the measuring electrode and associated electrode.

9. The electrochemical sensor defined in claim 1, wherein the housing comprises a gas cell and a gas-permeable diffusion membrane, wherein the gas-permeable diffusion membrane is located between the gas cell and the measuring electrode.

10. The electrochemical sensor defined in claim 1, wherein the gas to be quantified is ionized at the measuring electrode to form ions, and the electrolyte contains the ions which are generated in the gas ionization at the measuring electrode.

11. The electrochemical sensor defined in claim 1, wherein the sensor further comprises a reference electrode.

12. The electrochemical sensor defined in claim 1, wherein the sensor further comprises a supplement electrode.

13. The electrochemical sensor defined in claim 1, wherein the sensor comprises at least two measuring electrodes.

14. The electrochemical sensor defined in claim 1, wherein the electrolyte is a solid electrolyte comprising a polymer comprising an electrolytic solution.

15. The electrochemical sensor defined in claim 14, wherein the solid electrolyte comprises a polymer prepared by polymerization of at least one monomer and an electrolytic solution.

16. The electrochemical sensor defined in claim 15, wherein the monomer is methylmethacrylate, the electrolytic solution comprises at least one acid, and the solid electrolyte further comprises a polymerization initiator.

17. The electrochemical sensor defined in claim 16, wherein the electrolytic solution comprises at least one acid selected from the group consisting of sulfuric acid, trifluoromethane sulfonic acid and phosphoric acid.

18. A method for quantifying at least one gas, comprising:

providing an electrochemical sensor comprising a housing, a measuring electrode located within the housing and comprising a catalytic material which causes a reaction of the gas to be quantified, an associated electrode located within the housing and comprising a carbonaceous material, and an electrolyte in contact with the measuring and associated electrodes, wherein the carbonaceous material in the associated electrode has a specific surface of at least 40 $m^2/g$ and comprises reversibly oxidizable or reducible electrochemically active surface compounds;

exposing the electrochemical sensor to the gas to be quantified;

setting an external voltage across the measuring electrode and the associated electrode; and measuring the current flowing between the measuring electrode and the associated electrode to quantify the gas to be quantified.

19. The method defined in claim 18, wherein the gas to be quantified is selected from the group consisting of hydrogen, oxygen, carbon monoxide and silane.

20. The method defined in claim 18, wherein the gas to be quantified is hydrogen, the measuring electrode comprises platinum, the associated electrode comprises activated carbon with a specific surface of 1000 to 1,700 $m^2/g$, the electrolyte comprises a strong mineral acid, and the external voltage is about 0.3 volts.

21. The method defined in claim 18, further comprising regenerating the electrochemical sensor, after said measuring step, by reversing the external voltage set across the measuring electrode and the associated electrode.

22. An electrochemical sensor to determine a gas concentration of a gas to be quantified, comprising:

a housing comprising apertures for electrode terminals and a gas cell having intake apertures, a measuring electrode located within the housing and comprising a catalytic material which causes a reaction of the gas to be quantified, an associated electrode located within the housing and comprising a carbonaceous material, an electrolyte in contact with the measuring and associated electrodes, and an electrical means for applying a voltage across the measuring electrode and the associated electrode, the electrical means having electrode terminals located in the apertures in the housing, wherein the gas cell allows the gas to be quantified to contact the measuring electrode, and wherein the carbonaceous material in the associated electrode has a specific surface of at least 40 $m^2/g$ and comprises reversibly oxidizable or reducible electrochemically active surface compounds.

* * * * *